Sept. 26, 1961 P. T. JAMES Plant Pat. 2,094
CLEMATIS PLANT
Filed April 13, 1960
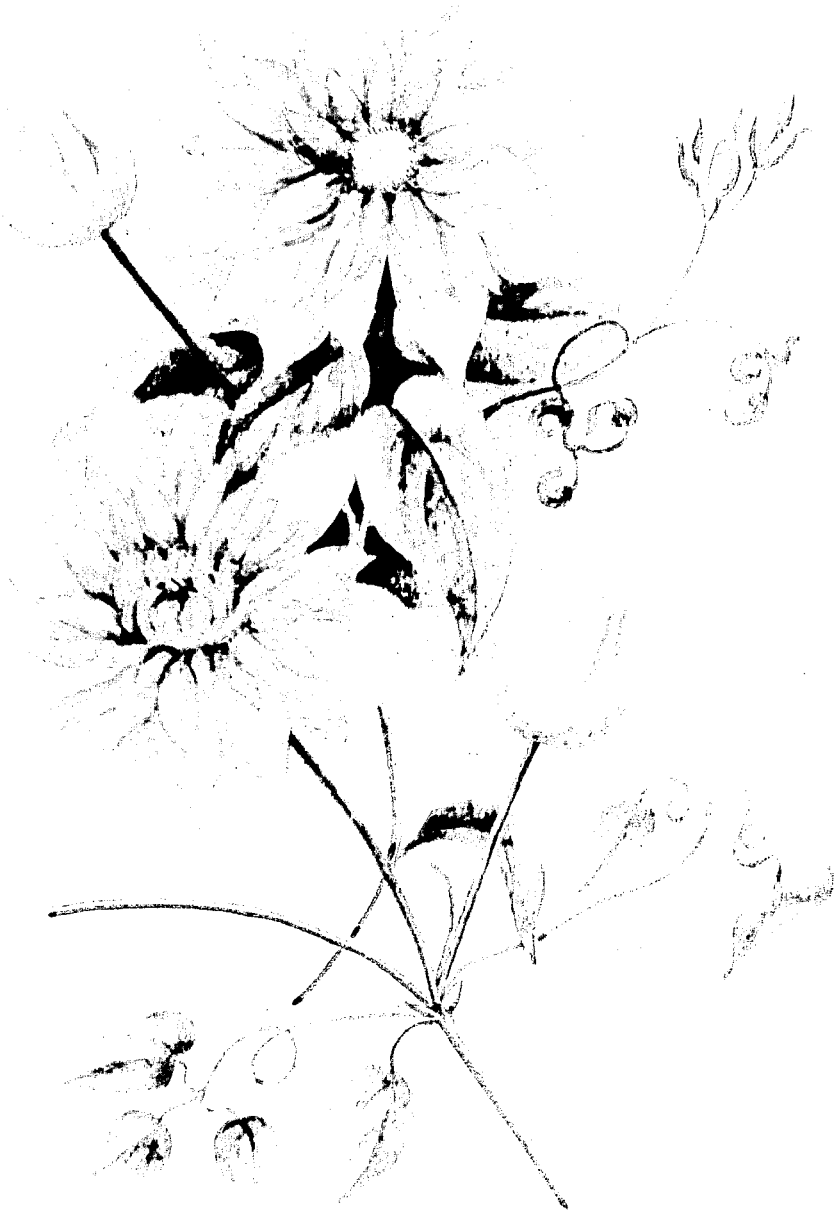
WITNESS
Addison E Avery
INVENTOR
Percival Thomas James, deceased,
by Percival George James, administrator,
by: John H Richards,
ATTY.

United States Patent Office

Plant Pat. 2,094
Patented Sept. 26, 1961

2,094
CLEMATIS PLANT

Percival Thomas James, deceased, late of Kelowna, British Columbia, Canada, by Percival George James, administrator, Kelowna, British Columbia, Canada, assignor to The Wayside Gardens Company, Mentor, Ohio Filed Apr. 13, 1960, Ser. No. 22,070
1 Claim. (Cl. 47—60)

This invention relates to a new variety of double Clematis plant.

The present Clematis was discovered by the decedent growing in his cultivated garden in Duncan, British Columbia.

It is believed to be a chance seedling from a cross between a *Clematis jackmani* plant and a double white Clematis plant, both of which were growing therein.

The new variety was asexually reproduced by soft wood cuttings, layering, and root divisions, at Duncan, British Columbia.

The drawings show in color a number of typical stalks with flowers, leaves and buds.

In designating colors herein, the British Color Council Horticulture Color Chart and the Maerz and Paul Dictionary of Color are used. References to the former are designated "Sheet," followed by the proper numerals. References to the latter are designated "Plate," followed by letter and number.

*Roots*

The roots are fleshy, clustered, and large for this type of plant. The plant is generally deep rooted, the roots having less spread than the upper exposed portion of the plant. The plant roots have good resistance to drought and wetness. Their winter resistance is exceptional. They have survived temperatures of 24° below zero in ice. They do well in either alkaline or acid soils.

*Exposed plant structure*

The exposed plant is a fairly hardy perennial spreading vine with very dense foliage. The plant is a vigorous grower, a two or three year old plant growing from five to ten feet in one season. The plant as a whole has the usual contour. The exposed plant withstands temperatures of zero and up when protected. When it is unprotected, severe frosts kill the exposed portion back to the roots. The exposed plant has good drought and wet resistance. It prefers intense heat but will tolerate partial shade. It is indifferent to exposures in warm climates, but in colder climates prefers an east or south exposure. It grows well in normally drained alkaline or acid soil, and particularly well in loam and clay.

*Individual parts of exposed plant*

The main stalks are slightly branched climbing vines which are relatively brittle. They are generally adequate to support the foliage and blooms well.

They are from five to ten or more feet in length on the average. They are smooth textured and grow in groups from the roots. The branches are oppositely arranged and numerous in quantity. Generally, they are quite brittle but adequate to support the blooms and foliage. They also are vine-like.

The foliage is relatively dense and very abundant, the leaves being arranged oppositely. The new leaves are a medium green on the top and bottom, as also are the old leaves, Plate 19–L–7. Their color is quite uniform.

The leaves are of the usual shape, the main leaves ranging in length from about two inches to three inches. The side leaves have a minimum length of about two inches and vary in width from one and one-half inches to two inches. They are generally lanceolate-ovate, having an entire margin divided into three, and acute apices. They are generally thin with smooth upper and lower faces. Their persistency on the plant is excellent. In general, they are extremely dense and protect the plant in winter, falling off in spring after the buds are well formed.

The petioles are a reddish brown and green and of smooth surface texture. They average about two inches in length and are strong. There are no stipules.

*Bloom*

The plant blooms well in temperate or sub-tropical zones and prefers a fairly frost free location for the best results. It blooms best in the sun, but will bloom well in shade in warm climates. It blooms best in an easterly and southerly exposure, though it does quite well in a western exposure. It blooms best in a dry season, though it does fairly well in wet or hot seasons, and in a rich, well drained, but moist or damp acid, alkali or neutral soil. Clay, loam, sandy loam, and clay loam soils all are satisfactory. The quality of the blooms is best in sun or partial shade, as also is the quantity. The color tends to deepen to a deeper mauve in alkaline soils and with sun and heat.

The plant produces a mass of double blooms in May and June in sunny exposures with moderate warmth and moisture. The blooms are very large if the weather is not too hot. The color varies, being brighter and deeper in sun and alkaline soil, the shades becoming softer in damp soils or shady locations.

The double blooms appear on the plant on the second year wood for a period of about two months. As the vigorous new growth starts, the blossoms are single. These single blossoms continue at the ends of the new growth until heavy frost.

The buds generally are terminal and lateral, quite large, and relatively plump and globular on the double blooms and more elongated on the single blooms. In aspect they are slightly pubescent. They are supported in upright position. They have no petaloid sepals, but the petals are green and mauve on the outside when blooming starts. When the petals begin to unfurl, they are mauve and blue. When half grown, they are blue shading to lighter tips.

The peduncles average from 2 inches to 4 inches in length, have slightly fuzzy surfaces, and vary from green to reddish in color. They are relatively strong.

The buds remain closed for a long time if the weather is cold, but open rapidly in warm weather.

The blooms average from 5 inches to 7 inches in diameter. The plant bears very heavily, the number of double blooms increasing with age. They are borne both singly and in pairs. They are long lasting on the plant but last only a short period when cut. On the double blooms, there are from 40 to 50 petals, on the single blooms, from 6 to 9. The petals vary in color from a middle blue to mauve, depending upon the heat and soil. The base of the petals is blue. The outer petals are slightly lighter in color on the double flowers. Slightly green streaks sometimes occur in the outer petals. The reverse of the petals has lighter blue streaks up to the center line. In the center of the bloom, there are thick clusters of yellow stamens.

The petals have a tendency to lighten with age. There is no great discoloration otherwise. The petals are smooth, but slightly crinkled. On the under surface, they are streaked white and blue up to the center. Quite generally the single petals have a smooth raised ridge running up the center. They are arranged in the usual fashion and the flowers are free from petaloids. Their persistence uncut is excellent but only fair if cut unless floated. The general tonality of the plant from a distance may be designated a Wedgwood blue.

The stamens are arranged in a thick cluster and have white filaments about ½ inch long. The pollen color is yellow. The styles are about the same length as the filament and greenish white in color. The stigmas are of usual shape and greenish white.

Some of the largest outermost petals of the back or outside row have small nearly white areas at the ends, tipped with pale green, comparable to Plate 19–J–2, whereas others do not.

The color of the petals ranges from sea lavender violet Sheet 153, No. 637/3 to heliotrope Sheet 82, No. 636/1 through violet Sheet 36, No. 36/1. Due to the compact arrangement of the stamens, the pollen forms a thick yellow mass at the center of the bloom, comparable to canary yellow, Sheet 2, No. 2/2.

The distinguishing characteristics or qualities of the plant are the very beautiful double blooms and the period during which the double and single blooms occur, the double blue flowers appearing first on the last year growth, growing in profusion during May and June, and being followed by, or mingled with, large single blooms on the new growth which continue until heavy frost.

Another important characteristic of the plant is the heavy dense foliage which, if not pruned back, gives excellent protection to the plant during the winter months and drops off in the spring, insuring survival of the one year old growth and double blooms thereon the second year.

Another important feature is the extreme hardiness of the roots.

Having thus shown and described the new variety of Clematis plant, what is claimed is:

A new and distinct variety of Clematis plant substantially as herein shown and described.

No references cited.